United States Patent [19]
Watanabe et al.

[11] Patent Number: 5,324,431
[45] Date of Patent: Jun. 28, 1994

[54] PROCESS FOR TREATING SUSPENDED SUBSTANCES IN LIQUOR

[75] Inventors: Shoji Watanabe; Kenji Baba; Ichiro Enbutsu; Hayao Yahagi; Harumi Matsuzaki, all of Hitachi; Mikio Yoda, Ibaraki; Naoki Hara; Yoshikatsu Asada, both of Hitachi, all of Japan

[73] Assignee: Hitachi, Ltd., Tokyo, Japan

[21] Appl. No.: 571,924

[22] Filed: Aug. 24, 1990

[30] Foreign Application Priority Data
Aug. 25, 1989 [JP] Japan .................. 1-217359

[51] Int. Cl.⁵ .................................. C02F 3/02
[52] U.S. Cl. ........................ 210/614; 210/709; 210/745

[58] Field of Search ........... 210/745, 614, 609, 630, 210/631, 709, 800, 903, 906

[56] References Cited

U.S. PATENT DOCUMENTS

| | | | |
|---|---|---|---|
| 4,564,444 | 1/1986 | Hiraoka et al. | 210/614 |
| 4,650,585 | 3/1987 | Hong et al. | 210/614 |
| 4,867,886 | 9/1989 | Botkins, Jr. | 210/745 |
| 5,021,166 | 6/1991 | Torpey | 210/745 |
| 5,037,559 | 8/1991 | Schmitt | 210/745 |

Primary Examiner—Thomas Wyse
Attorney, Agent, or Firm—Antonelli, Terry, Stout & Kraus

[57] ABSTRACT

Suspended substances, such as active sludge, in a liquor is treated in an apparatus for treating the liquor by predicting a suspension state on the basis of an amount of existing suspended substances in the liquor.

6 Claims, 7 Drawing Sheets

PROCESS FOR TREATING SUSPENDED SUBSTANCES IN LIQUOR

BACKGROUND OF THE INVENTION

1) Field of the Invention

This invention relates to a process and an apparatus for treating suspended substances such as active sludge, flocs, etc. in a liquor. The present invention is applicable to sewage treatment plants for treating organic substances suspended in a sewage with active slude, to waterworks for making drinking water by purifying the raw water from rivers, to culture plants for culturing microorganism, bacteria and yeasts, to plants for producing lactobacillus such as chlorella, etc. and medicines such as penicillin, etc., to plants for filtering suspended substances in a liquor, to dephosphorizing plants for removing phosphorus components contained in water, etc.

2) Prior Art

In waterworks and sewage treatment plants, it is a general practice to purify water by precipitating suspended substances in a liquor, such as active sludge, etc. by gravity. When the suspended substances in a liquor are not precipitated or the precipitation state is deteriorated, the suspended substances flow out together with treated water, thereby deteriorating the water quality.

Heretofore, the coagulation state of the suspended substances has been visually observed or measured by manual analysis, and the settlability has been evaluated by the experiences and the sixth sense of operators on the basis of the thus obtained results. The present inventors have proposed a process for judging the precipitation state of active sludge at the time point of measurement by image-processing the existing state of coagulating microorganisms (zoogleal microorganisms) and filamentous microorganisms in a sewage treatment plant. The process is disclosed in Japanese Patent Application Kokai (Laid-open) No. 60-31886. The present inventors have also proposed a process for evaluating the precipitation state at the time point of measurement by determining the settlability of flocs from the luminance information of flocs obtained by image processing. The process is disclosed in Japanese Patent Application Kokai (Laid-open) No. 60-31886.

According to the above-mentioned prior art, only the settlability at the time point of measurement is judged. In other words, even if the settlability is good at the time point of measurement, it is impossible to tell how the settlability will be in the future. It is too late to take further steps after poor settlability has been recognized.

It is really necessary to evaluate at the time point of measurement what direction the precipitation state will take in the future and then take appropriate steps.

The above-mentioned prior art fails to provide a process for predicting the future precipitation state, and thus cannot predict the future precipitation state.

SUMMARY OF THE INVENTION

An object of the present invention is to provide a process and an apparatus for treating suspended substances in a liquor with a capacity for predicting a future precipitation state.

Another object of the present invention is to provide a process and an apparatus for treating suspended substances in a liquor by predicting a future precipitation state of the suspended substances on the basis of the existing state of suspended substances at the time point of measurement, thereby carrying out appropriate operation control.

These objects of the present invention can be attained by a process for treating the substances suspended in a liquor, which comprises predicting a suspension state on the basis of an amount of existing substances suspended in the liquor.

It is preferable to predict the suspension state on the basis of differences in amounts of existing substances suspended in the liquor at time intervals. Specifically, it is desirable to predict the suspension state by determining amounts of existing substances in the liquor at time intervals, thereby determining changes in the amounts with time, and making the change in the amounts with time correspond to a correlation obtained in advance between the amounts and the suspension states of existing suspended substances.

It is desirable to determine the amounts of the existing suspended substances at least at one time interval, thereby determining a change in the amounts of the existing suspended substances with time.

In cases of waterworks or sewage treatment plants, it is desirable to determine the amounts of the existing suspended substances at least at one time interval of a few hours to a few tens of hours, thereby determining a change in the amounts of the existing suspended substances with time.

It is desirable to determine the amounts of the existing suspended substances at least at one time interval at the same position or substantially at the same position, thereby determining a change in the amount of the existing substances with time. After the suspension state is predicted in this manner, it is desirable to control factors effecting the suspension state of the suspended substances.

In case of treatment of active sludge suspended in a liquor, it is desirable to predict settability of the active sludge by using a ratio of an amount of existing coagulating microorganisms on the active sludge to that of existing filamentous microorganisms on the active sludge as an evaluation index.

More specifically, it is desirable to control factors affecting the settlability of active sludge by picking up images of the active sludge, processing the thus obtained images as pieces of pickup information, thereby determining average particle size and volume of existing coagulating microorganisms and length of existing filamentous microorganisms, determining a change in an evaluation index with time by using a ratio of length of existing filamentous microorganisms to average particle size and volume of existing coagulating microorganisms as the evaluation index, and making the thus obtained change in the evaluation index with time correspond to a correlation obtained in advance between the evaluation index and the settlability of the active sludge, thereby predicting a precipitation state.

It is desirable to express an amount of the existing active sludge as a ratio of (average particle size of coagulating microorganisms)$^n$/(length of filamentous microorganisms/volume of the coagulating microorganisms), express a settlability of the active sludge as a volume of precipitated active sludge per unit weight, and make a change in the amount of the existing active sludge with time correspond to a correlation therebetween.

It is most desirable to express the amount of the existing active sludge as a ratio of (average particle size of coagulating microorganism)$^2$/(length of filamentous microorganism/volume of the coagulating microorganisms), express a settlability of the active sludge as a volume of precipitated active sludge per unit weight, and making a change in an amount of the existing active sludge with time correspond to a correlation therebetween.

Figure 10:
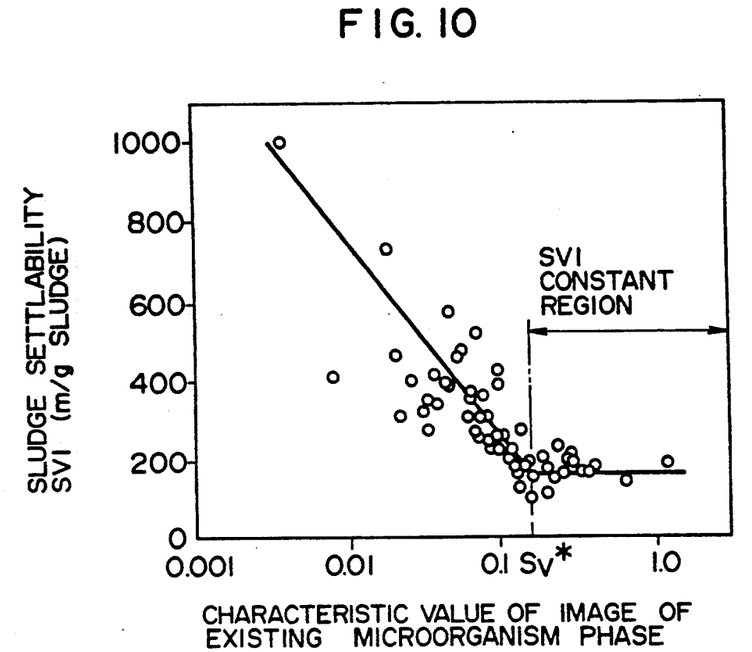
FIG. 10 is a diagram showing correlation between the evaluation index and the sludge settling characteristics.

The present invention is based on the investigation that there is a very close correlation between the amount of existing active sludge expressed as the above-mentioned ratio of (average particle size of coagulating microorganisms)$^2$/(length of filamentous microorganism/volume of coagualting microorganisms) and the settability of the active sludge expressed as the volume of precipitated active sludge per unit weight. Specifically, as shown in FIG. 10 which follows, the present invention is based on the investigation that the settlability of active sludge expressed as the volume of active sludge per unit weight is constant or substantially constant to show a good precipitation state when the amount of the existing active sludge expressed as the ratio of (average particle size of coagulating microorganisms)$^2$/(length of filamentous microorganisms/volume of coagulating microorganisms) is within a specific region.

Thus, even if the precipitation state is good at the time point of measurement, it is possible to predict how a future precipitation state will be, by determining a change in the amount of existing active sludge with time, and thus the necessary steps can be taken at the time point of measurement.

The amount of existing active sludge can be expressed as other formulae than the above, as given below:

(1) (average particle size of coagulating microorganisms)$^n$/(length of filamentous microorganism)
(2) (average particle size of coagulating microorganisms) $\times$ (length of filamentous microorganisms)
(3) (average particle size of coagualting microorganisms)$^n$/log (length of filamentous mi­crooganisms/volume of coagulating microorganisms)
(4) log (length of filaments microorganisms/volume of coagulating microorganisms)/(average particle size of coagulating microorganisms)$^n$ It is also possible to express filamentous microorganisms not in terms of their length, but their volume. It is also possible to express the coagulating microorganisms as their area in place of the average particle size.

In case of applying the present invention to a process for culturing microorganisms, cells, or yeast, it is desirable to predict a reaction state on the basis of changes in amounts of existing microorganisms, cells or yeasts with time, thereby controlling factors affecting the reaction state.

In case of applying the present invention to a process for propagating filamentous microorganisms in a liquor by making the microorganism grow in a liquor, followed by separation and purification, and repeating the foregoing steps, it is desirable to predict the propagation state of the microorganisms on the basis of changes in amounts of existing filamentous microorganisms with time.

In case of applying the present invention to a process comprising repetitions of a step of passing a liquor containing suspended substances through a filtration means and a step of back-washing the filtration means, it is desirable to determine sizes of the suspended substances in the liquor after passing through the filtration means, and predict a capacity for removing the suspended substances on the basis of changes in the sizes with time.

In case of applying the present invention to a process comprising adding crystal seeds to a liquor containing phosphorus, and crystallizing out the phosphorus on the surface of the seed crystals, thereby removing the phosphorus, it is desirable to determine a releasing amount of the crystallized phosphorus and predict a capacity for removing the phosphorus on the basis of changes in the releasing amount with time.

In case of applying the present invention to a sewage treatment plant provided with an aeration tank for aeration with an oxygen-containing gas and treating organic matters in sewage with active sludge and a settling pond for solid-liquid separation of the active sludge, it is desirable to predict the settlability of the active sludge, using an amount of existing active sludge as an evaluation index.

An example of the present apparatus for treating suspended substances, which comprises a mixing pond for coagulating substances suspended in a liquor by adding a coagulating agent thereto and a settling pond for settling the coagulated suspended substances, has a means for predicting the settlability of the suspended substances, using an amount of existing suspended substances as an evaluation index.

An example of the present sewage treatment plant, which comprises an aeration tank for aeration with an oxygen-containing gas and treating the organic matters in the sewage with active sludge and a settling pond for solid-liquid separation of the active sludge, has an image pickup means for picking up image of existing active sludge through enlargement or magnification, a means for determining an amount of existing coagulating microorganisms and an amount of existing filamentous microorganisms from the picked-up image information by image processing and a means for predicting the settlability of the active sludge, using a ratio of the amount of the existing coagulating microorganisms to that of the existing filamentous microorganisms as an evaluation index.

Furthermore, an example of the present sewage treatment plant, which comprises an aeration tank for aeration with an oxygen-containing gas and treating the organic matters in the sewage with active sludge and a settling pond for solid-liquid separation of the active sludge, has an image pickup means for picking up images of the active sludge through enlargement or magnification, a means for determining average particle size and volume of existing coagulating microorganisms and length existing filamentous microorganisms on the active sludge from the picked-up image information by image processing, and a means for predicting the settability of the active sludge, using a ratio of average particle size and volume of the existing coagulating microorganisms to length of the existing filamentous microorganisms as an evaluation index. As a result of investigations of the settlability of the active sludge in the sewage treatment in various ways, the present inventors have found that there is a correlation between the amount and the settlability of the existing active sludge and the settlability can be predicted by determining the amount of the existing active sludge. Specifically, it has been found that the settlability can be predicted by separating and extracting a liquid phase region and an active sludge region from a liquid mixture of active sludge for image processing, determining an average particle size of floc-forming microorganism, an amount of existing filamentous microorganisms and an amount of the active sludge from the extracted active sludge region, and determining a tendency of an evaluation index to increase or decrease, using a ratio of (the amount of the existing filamentous microorganisms and the amount of the active sludge to square of the average particle size of the floc-forming microorganisms.

Furthermore, it has been found that the reliability of predicting the settlability can be more enhanced corresponding to changes in the state of active sludge by taking a difference in the luminance between the liquid phase region and the active sludge region into the evaluation index. Since a bulking phenomenon, that is, deterioration of sludge settlability, can be predicted earlier in advance by the evaluation index, it is possible to take the necessary steps for the bulking phenomenon.

In order to judge whether to take such steps or not, operation assistance by operators is desirable by utilizing number of flocs and particle sizes of floc as pieces of image computation information.

Thus, according to the present invention, it is possible to predict the suspension state of suspended substances such as settlability, floatability, etc. from the amount of existing suspended substances in a liquor, as explained above. Thus, the present invention successfully provides a water treatment plant with a function to predict a suspension state of suspended substances.

The present inventors have confirmed that the settlability of suspended substances can be predicted by determining, specifically, average particle size and volume of existing coagulating microorganisms and length or volume of existing filamentous microorganisms as amounts of existing suspended substances and using these as an evaluation index.

The present inventors have found that the settability of active sludge can be predicted with a very high reliability by using a ratio of length of the existing filamentous microorganisms to the average particle size and volume of the existing coagulating microorganisms, whereby specific procedures for predicting the settlability of active sludge can be established.

PREFERRED EMBODIMENTS OF THE INVENTION

One embodiment of the present invention will be explained below, referring to FIG. 1.

Figure 1:
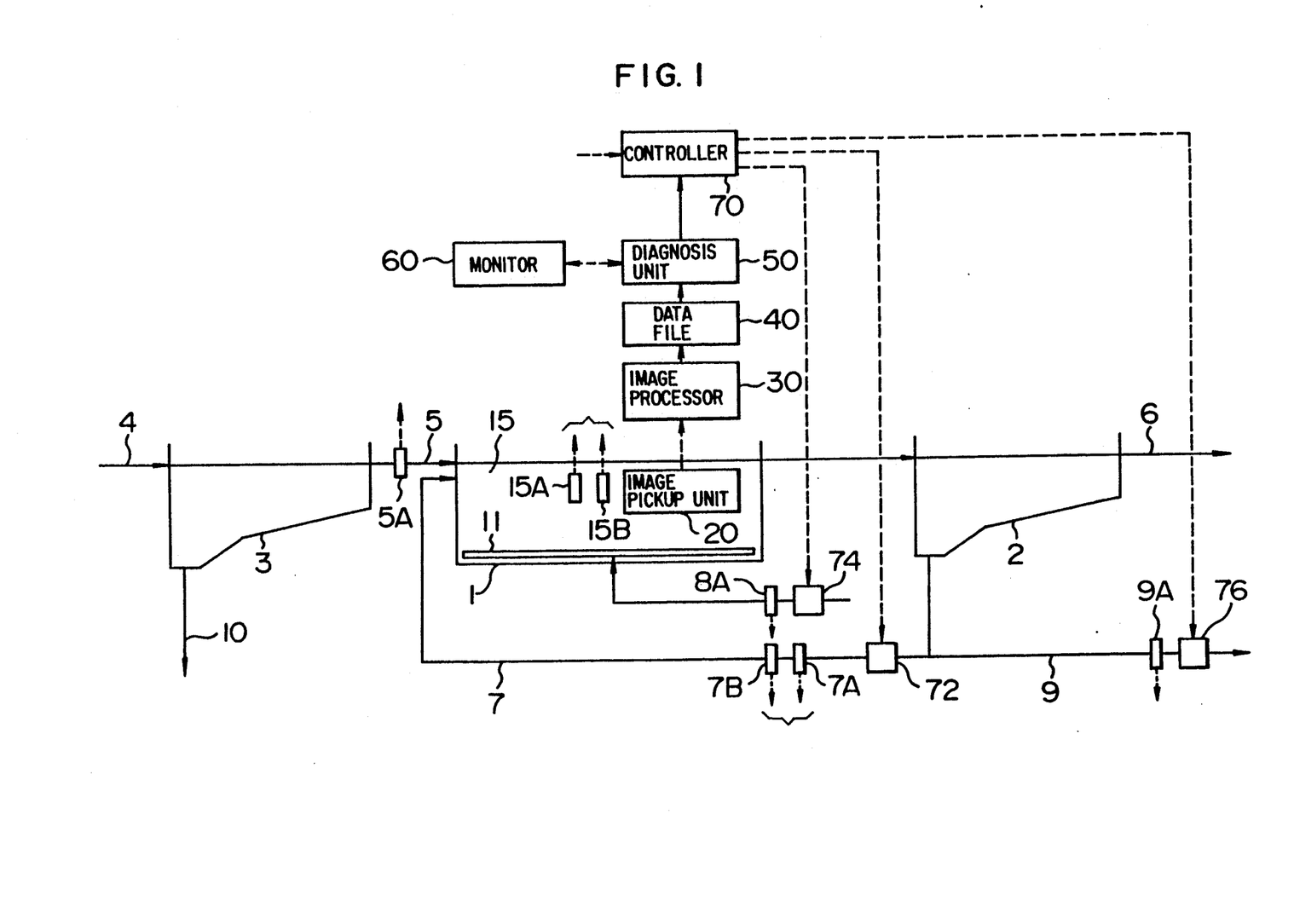
FIG. 1 is a schematic flow diagram according to one embodiment of the present invention.

FIG. 1 shows one example of applying the present invention to a sewage treatment plant using active sludge.

At first, the treatment functions will be briefly explained.

Sewage discharged from home, factories, etc. is treated through a pretreatment process (not shown in the drawing) to remove coarse ingredients, and then led to a first settling pond 3 as raw water 4 to precipitate the suspended solid matters, not removed through the pretreatment, by gravity. The precipitated matters are withdrawn from the pond 3 to the outside as raw sludge 10, which is concentrated, dehydrated, dried, incinerated, etc. in a sludge-treating plant (not shown in the drawing).

On the other hand, the supernatant is led to an aeration tank 1 from the settling bond as influent water 5 and made into a liquid mixture 15 with microorganisms called "active sludge". The liquid mixture 15 is stirred by air 8 injected from an air diffuser 11 provided at the bottom of the aeration tank 1 and supplied with oxygen at the same time, and the contaminant substances in the liquid mixture 15 are treated through the action of active sludge. For example, the organic matters are converted to carbon dioxide and water, and ammoniacal nitrogen is oxidized into nitric state or nitrous state nitrogen compounds, whereas the active sludge itself is propagated spontaneously at the same time. In this process, phosphorus is taken into the active sludge. The liquid mixture 15 leaving the aeration tank 1 as an effluent is led to a final settling poind 2 to precipitate the active sludge by gravity, and the resulting supernatant is discharged to river, etc. as treated water 6 after a sterilization treatment (not shown in the drawing).

On the other hand, the settled active sludge is highly concentrated, and most of the settled active sludge is recycled to the aeration tank 1 as return sludge 7, and the remaining portion thereof, which corresponds to the propagation increment, is discharged to the outside as excess sludge 9, and treated in the same manner as the raw sludge 10 is done. Or, the excess sludge 9 is once led to the initial settling pond 3 and discharged to the outside together with the raw sludge 10, depending upon conditions of sewage treatment plants. The raw water 4 may be directly led to the aeration tank 1 in case there is no initial settling pond 3 or without passing through the initial settling pond 3.

In the foregoing sewage treatment plant, control of active sludge is one of important operating duties, where particularly a maintenance control for forming active sludge with a good settlability is required. Deterioration of settlability of active sludge is called "bulking", which will not only increase a fear of sludge outflow from the final settling pond 2, but will also place a heavy burden on the aeration treatment functions, particularly sludge treatment function. Maintenance of active sludge with a good settlability can eliminate such a fear. Thus, it is very effective to determine the settling characteristics of active sludge and detect a sign of deterioration or predict the sign earlier in advance.

The present invention provides a process for predicting the bulking phenomenon and also an operating control system based on the prediction from this point of view.

The present invention will be described in detail, taking into account this point of view.

Numeral 20 is an image pickup unit for observing the liquid mixture 15, which is dipped into the aeration tank 1. It is desirable that the image pickup unit 20 has an optical image-enlarging or magnifying mechanism capable of judging microorganism phases existing on the active sludge, a TV camera for making the luminance information of the enlarged optical image into electric signals, an illuminating mechanism capable of illuminating the liquid mixture 15 as an image pickup target with a light, and a liquid mixture-exchanging mechanism. The TV camera either of monochromatic type or color type can be used. The density-varied image (original image) of a portion of the liquid mixture 15 as a target, obtained by the image pickup unit 20 is output into an image processor 30 as analog signals that reflect the brightness. It is possible to branch the signals output from the image processor 30 and display the signals on a monitor TV, though not shown in the drawing.

Figure 2:
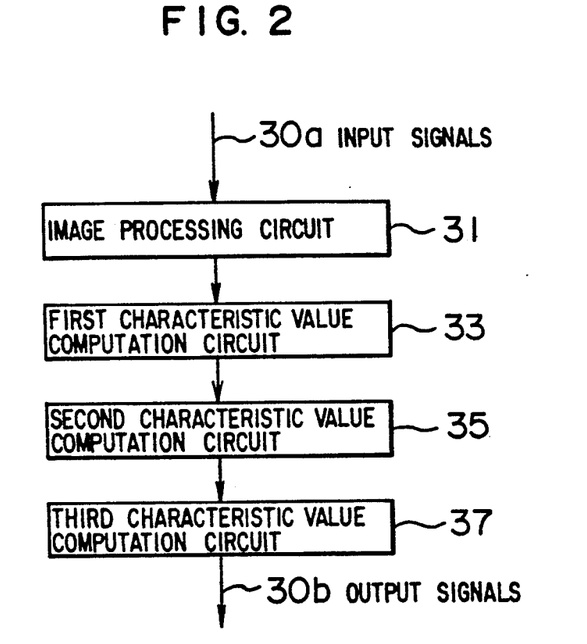
FIG. 2 is one example of procedure for computing the characteristic values of active sludge.
Figure 3:
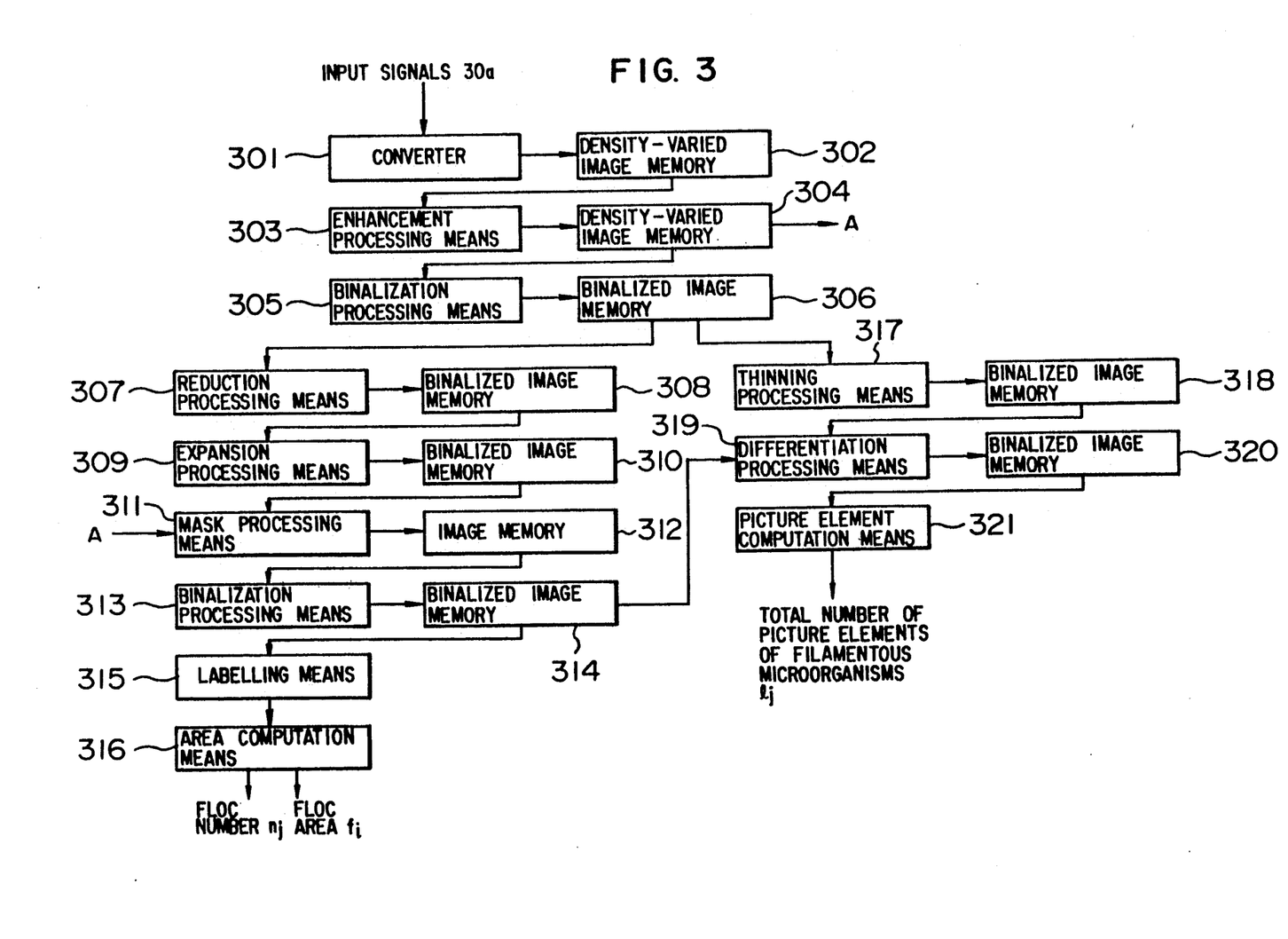
FIG. 3 is a flow chart showing one example of procedure for separating and recognizing the microorganism phase from active sludge.

The image processor 30 recognizes and computes the characteristic values of microorganism phase existing on the active sludge from the input density-varied images through a series of processing, one example of which is shown in FIG. 2. At first, the input signals 30a are subjected to extraction of the microorganism phase and computation of number of picture elements by an image processing circuit 31. One example of the processing procedures is shown in FIG. 3. The input signals 30a (analog signals) are convented to digital signals by a converter 301 and the digital signals are stored in a density-varied image memory 302, which has a storing area constituted, for example, by 256×256 picture elements, and each picture element of the stored image has luminance information g (i, j) correspodning to a brightness.

Microorganisms existing on the active sludges generally include floc-forming microorganisms, filamentous microorganisms and protozoa, among which the former two deeply take part in the sludge settleability.

Figure 4:
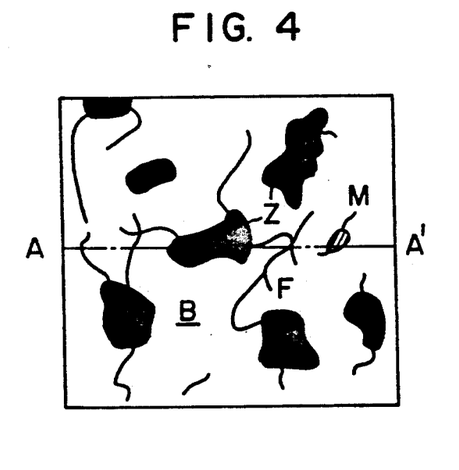
FIG. 4 is a sketch showing one example of pickup image of active sludge-mixed liquor.
Figure 5:
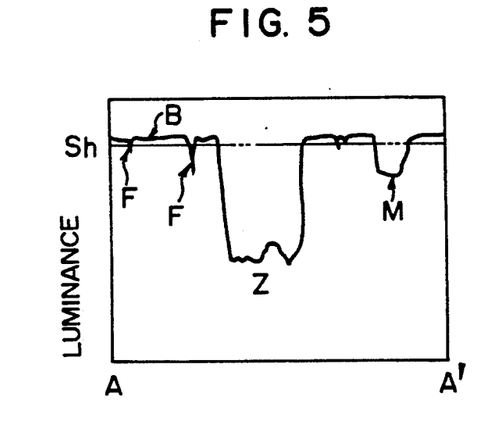
FIG. 5 is a diagram showing one example of luminance distribution scanned along the line A—A' of FIG. 4.
Figure 6:
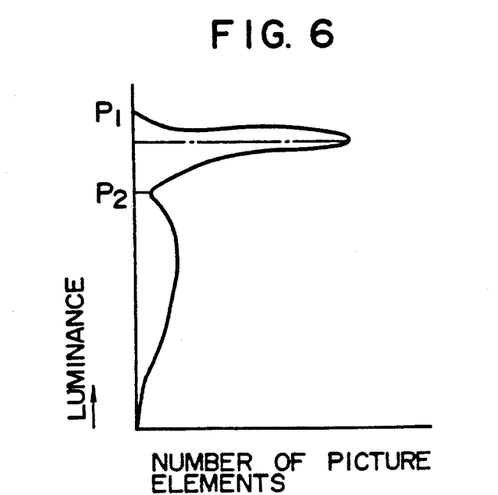
FIG. 6 is a diagram showing correlation between the luminance and the number of picture element directed to FIG. 4.

FIG. 4 shows one example of density-varied image g (i, j) of an active sludge suspension when the optical image-enlarging or magnifying mechanism is in focus in the image pickup unit 20 using a transmitted light as an illumination source, and FIG. 5 is a luminance distribution diagram scanned along the line A—A' of FIG. 4, showing that the liquid phase region B is high and the luminance is lowered in the order of filamentous microorganisms F, protozoa M and floc-forming microorganism Z. The density varied image of image memory 302 is subjected to a filtering processing by an enhancement processing means 303 to make clear the interface between the liquid phase region and the active sludge region, thereby adjusting the luminance. The thus adjusted density-varied image g' (i, j) is stored in a density-varied image memory 304. In the adjustment of luminance by the enhancement processing means 303, it is important to make particularly clear the filamentous microorganisms F having a small difference in the luminance from the liquid phase region. This can be done with a space filter constituted by, for example, 3×3 picture elements. By the adjustment of luminance, various microorganism phases can be effectively image-extracted with high exactness. Then, the adjusted density-varied image g' (i, j) is input into a binalization processing means 305 and subjected to a processing given by the following formulae, using a given luminance level Sh as a standard to separate and extract the existing area of active sludge [B (i, j)=1] and the liquid phase region [B (i, j)=0].

$$\left. \begin{array}{l} g'(i,j) \leq Sh \ B(i,j) = 1 \\ g'(i,j) > Sh \ B(i,j) = 0 \end{array} \right\} \quad (1)$$

The binalized images B (i, j) are stored in a binalized image memory 306. The given luminance Sh may be set, or varied corresponding to a frequency distribution of number of picture elements against the luminance called a histogram of adjusted density-varied image g' (i, j). In the latter case, the luminance Sh may be at a level by a given value lower than the peak luminance level $P_1$ of liquid phase region B or at a luminance level $P_2$ showing a saddle part which exists below the liquid phase region B. By changing the luminance Sh, the active sludge can be extracted with high exactness even against changes in the illumination intensity of image pickup unit 20.

The binalized image B (i, j) is input into a reduction processing means 307, where region of information "1" is judged and reduced from the edge by one picture element after another. By this processing, filamentous microorganisms having a width of one or two picture elements are erased from the image, While leaving images of floc-forming microorganisms, etc. on the picture surface. The reduced image is written on a binalized image memory 308 and the input region of information "1" is expanded by one picture element after another along the entire circumference in an expansion processing means 309. At least one run each of these reduction and expansion processings must be carried out, but the run number of the reduction processing must be equal to that of the expansion processing. The expanded image is an image that extracts only the floc-forming microorganisms by erasing the filamentous microorganisms therefrom, and is stored in a binalized imaged memory 310. In a mask processing means 311, the expanded image and the adjusted density-varied image g' (i, j) are laid one upon another to partially extract the corresponding region of the adjusted density-varied image to the information "1" input region of the expanded image, followed by storing in an image memory 312.

The partially extracted image is subjected to the same processings as given by the formulae (1) by a binalization processing means 313 to exactly extract the floc region, followed by memorizing into a binalized image memory 314. The standard luminance Sh' in this binalization processing must be below Sh. A labelling means 315 labels individual flocs on the floc-extracted image and an area computation means 316 computes numbers of picture elements of individual number-labelled flocs to output number of flocs nj and individual floc areas fi (based on the picture elements) on the picture surface.

On the other hand, the binalized image B (i, j) written in the binalized image memory 306 is input into a thinning processing means 317 to extract all the lines having a width of one picture element without changing the length of extracted bodies, followed by storing in a binalized image memory 318. A differentiation processing means 319 computes a differential between the thinned image and the floc-extracted image stored in the binalized image memory 314, thereby erasing the floc regions and extracting only filamentous microorganisms. The filamentous microorganism-extracted image is memorized in a binalized image memory 320. A picture element computation means 321 makes an integral computation of input picture elements of information "1" on the filamentous microorganism-extracted image throughout the entire picture surface and outputs total number of picture elements of filamentous microorganisms lj. Output total number of picture elements lj corresponds to the length of existing filamentous microorganisms on the entirety of one picture surface, because all the line widths of extracted bodies on the thinned image are widths of one picture element.

In FIG. 3, various characteristic values of microorganism phase are extracted by direct processing of picked-up image 30a. However, a blank image free from the presence of active sludge can be memorized in the density-varied memory in advance, followed by differentiation between the blank image and the picked-up image 30a, and specific values are added to all the picture elements of the differentiated image to obtain a differentiated, density-varied image, which can be processed in the processing procedure of FIG. 3. By using the differentiated, density-varied image, unevenness in the intensity of the illuminating mechanism can be overcome, thereby effectively enhancing the extraction precision.

In the foregoing embodiment, the protozoa are recognized as a floc region, but it is not objectionable to obtain the number of flocs nj and area fi free from the protozoa. That is, the protozoa as motile organisms can be eliminated by subjecting the one and same liquid mixture to image pickup in a plurality of runs at given time intervals, subjecting the plurality of the picked-up image to differentiation treatment to extract the displaced area and eliminating the extracted area from the image to be computed. The elimination of protozoa is effective for exact extraction of features of floc-forming microorganisms.

Furthermore, the various processed images in the processing steps can be displayed on a monitor TV to observe or evaluate the state of extraction, and the set values of standard luminance Sh, etc. can be judged thereby. In that case, it is preferable to make synthetic display by color discrimination of extracted images for the individual microorganism phases, thereby making comparisons with the picked-up, density-varied images. The computation of total number of picture elements lj of filamentous microorganisms from the extracted image of filamentous microorganisms can be made after noise treatment in advance.

Number of flocs nj, individual floc area fi and number of picture elements of existing filamentous microorganisms lj per one picture surface output from the image processing circuit 31 are input into a first characteristic value computation circuit 33 to compute various characteristic values.

The quantity of existing filamentous microorganisms Lj (m/ml) can be obtained according to the following equation:

$$L_j = K_1 \cdot l_j \cdot l / v \qquad (2)$$

where l is an actual length per one picture element, v is a volume of a liquid mixture as a sample for the image pickup and $K_1$ is a constant.

On the other hand, the characteristic value of flocs is computed as in-plane radii i of individual flocs according to the following equation by assuming equivalent circles to the areas fi of picture elements of number-labelled individual flocs.

$$r_i = (4 \cdot f_i \cdot a_g / \pi)^{\frac{1}{2}} \qquad (3)$$

where $a_g$ is an actual field area per one picture element.

Figure 7:
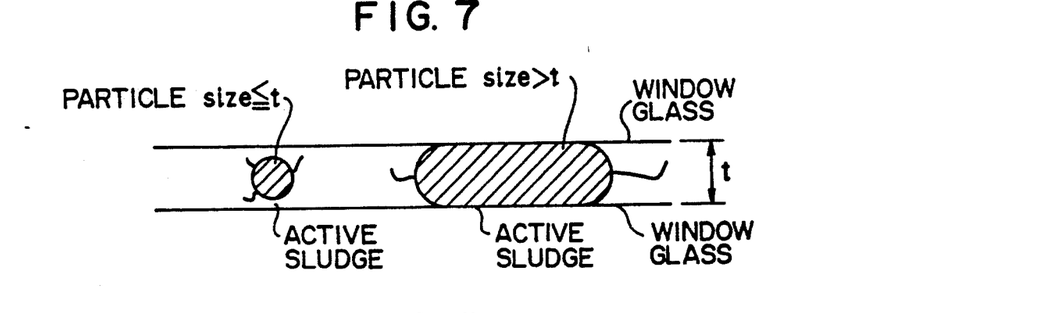
FIG. 7 is a view showing changes in the shape of active sludge.

In order to recognize the microorganism phases existing on the active sludge as the object of the present embodiment, it is necessary that the thickness of a liquid mixture susceptible to the image pickup in the image pickup unit 20 be not more than several hundred μm. The active sludge is in an aggregate state having a size of a few mm and thus the shape of active sludge varies, depending upon the thickness of the liquid mixture in the image pickup unit 20. The mode of change in the shape is shown in FIG. 7. That is, the active sludge having a size more than the liquid mixture thickness t takes a flat ball shape, resulting in changes in the in-plane radius. In that case, the volume vi taken by the active sludge can be presumed constant, and its free particle size $R_i$ can be calculated according to the following equations:

$$\begin{aligned} v_i &= \pi \cdot R_i^3 / 6 \\ &= \pi \cdot t (r_i - t)^2 / 4 + \pi^2 \cdot t^2 (r_i - t) / 8 \end{aligned} \qquad (4)$$

$$R_i = \{t (r_i - t)^2 / 24 + \pi \cdot t^2 (r_i - t)/48\}^{\frac{1}{3}} \qquad (5)$$

Number of flocs $N_j$ per unit volume can be obtained according to the following equation:

$$N_j = n_j / v \qquad (6)$$

From the number of flocs $N_j$ and the free particle size $R_i$, an average particle size $R_j$ on the processed picture surface can be calculated according to the following equation:

$$R_j = \frac{1}{N_j} \sum_{i=1}^{N_j} R_i \qquad (7)$$

Volume of flocs $V_j$ can be calculated according to the following equation:

$$V_j = \sum_{i=1}^{N_j} K_2 \cdot R_1^3 \qquad (8)$$

wherein $K_2$ is a computation constant.

The length $L_j$ of filamentous microorganisms, number of floc-forming microorganisms $N_j$, average particle size $R_j$ and volume $V_j$ per one processed picture surface are output to a second characteristic value computation circuit 35.

In the second characteristic value computation circuit 35, various characteristic values are computed for predetermined number P of processed picture surfaces. Predetermined number P of processed picture surfaces is set corresponding to the operating period of image processing circuit 31. For example, when the operating period is a time interval of one minute and computation information is to be output at time intervals of one hour, P is set to 60 (i.e. P=60). Though it is said that the state of active sludge changes slowly, it is preferable to set the number of processed picture images P so as to output computation information at least one time per day.

The second characteristic value computation circuit 35 has memory means for the various input characteristic values, and compute various characteristic values according to the following equations at every stage that the predetermined number P of processed picture surfaces has been counted to output signals 30b:

$$L(t) = \frac{1}{P} \sum_{j=1}^{P} L_j$$
$$N(t) = \frac{1}{P} \sum_{j=1}^{P} N_j$$
$$R(t) = \frac{1}{P} \sum_{j=1}^{P} R_j$$
$$V(t) = \frac{1}{P} \sum_{j=1}^{P} V_j$$
(9)

Length L(t) of filamentous microorganism, number of floc-forming microorganisms N(t), average particle size R(t) and volume V(t) from the second characteristic value computation circuit 35 are input into a third characteristic value computation circuit 37 to compute an evaluation index Sv(t) according to the following equation:

$$Sv(t) = \frac{R^2(t)}{(L(t)/V(t))}$$
(10)

The index is obtained only from image computation information. Individual image computation information and evaluation indices are stored in a data file 40.

Figure 8:
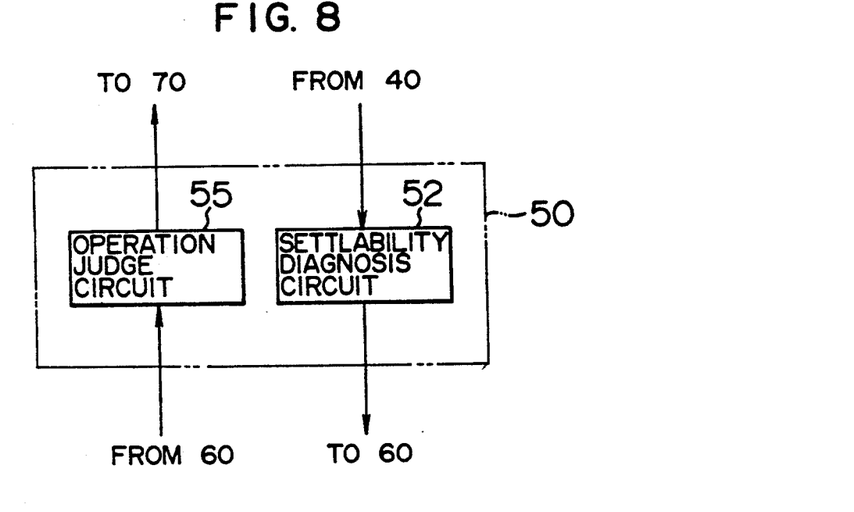
FIG. 8 is a block diagram showing how to evaluate image computation information.
Figure 9:
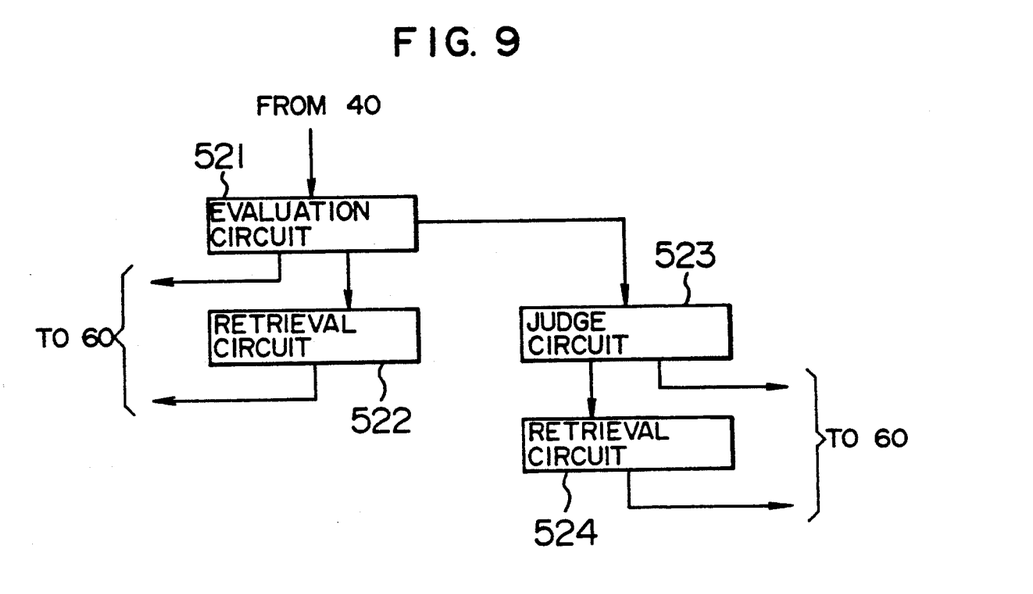
FIG. 9 is a block diagram showing how to evaluate the sludge settling characteristics.

Nuemral 50 is a diagnosis unit comprising a settlability diagnosis circuit 52 and an operation judge circuit 55, as shown in FIG. 8. The settlability diagnosis circuit 52 diagnoses the state of active sludge on the basis of the image computation information to judge factors for deterioration of settlability. One example of diagnosis procedure is shown in FIG. 9. Evaluation index Sv(t) is input into an evaluation circuit 521 to evaluate the settling characteristics of active sludge. As a result of extensive experimental studies made by the present inventors, it has been made possible to predict the sludge settlability from the evaluation index Sv(t) proposed by equation (10). The results are shown in FIG. 10, according to which SVI (sludge volume index) showing the sludge settlability as a settled volume per unit amount of active sludge after settling for a predetermined time lowers with increasing evaluation index Sv(t), showing a tendency to improve the settlability. Furthermore, it is apparent from FIG. 10 that there is a region where SVI is less changed against the evaluation index Sv(t). The region is called a SVI-constant region. Deterioration of sludge settlability, that is, bulking, means the case that SVI is generally more than 200-300 (ml/g.sludge). It has been found that the SVI-constant region in FIG. 10 is formed in a state of good settlability, which is not called "bulking". That is, this means that the sludge settlability can be evaluated by the proposed index and bulking can be predicted from its tendency to increase or decrease. Furthermore, the proposed evaluation index Sv(t) is in good agreement with Robinson's correlation equation generally known as an interfacial settling rate of suspended substances and thus is theoretically supported. In the Robinson's correlation equation, the settling rate u is expressed as particle size d of suspended particles, density difference $\Delta\rho$ and viscocity $\mu$, as given by the following equation:

$$u = k \cdot \frac{d^2 \cdot \Delta\rho}{\mu}$$
(11)

Since SVI is a volume of active sludge on the basis of the interface after a predetermined time, SVI can be regarded as a reciprocal number of the interfacial settling rate u. In other words, SVI can be expressed in the form of the foregoing equation and it seems that the correlation of equation (11) can be given by replacing the constituent factors with the image computation information. Thus, the present inventors proposed the equation (10) using free floc particle size R(t) for the particle size d and length of filamentous microorganism L(t) and floc volume V(t) per unit volume as factors for viscosity $\mu$ and density difference $\Delta\rho$ and tried to evaluate SVI. The results are the correlation given in FIG. 10. Why the length of filamentous microorganisms and floc volume were used as factors for the viscosity and density difference is that it was expected that the filamentous microorganisms had a role of inhibiting the coagulation of flocs themselves and increasing the frictional resistance, that is, an effect on an increase in the viscosity and a role of lowering the apparent density through protrusion of other miroorganisms than floc-forming microorganisms, and its degree would be influenced by the length of filamentous microorganisms against the floc volume. The correlation shown in FIG. 10 can be made into the following equation (12):

$$SVI = K_3(SV(t))^{-1}$$
(12)

That is, the correlation can be expressed in the same form as that of equation (11).

Thus, the evaluation circuit 521 judges a settlability by comparison between the evaluation index Sv(t) and the set value Sv* and outputs an alarm display of bulking to a monitor 60 when Sv(t)≦Sv*, and retrieves bulking factors through a retrieval circuit 522. The set value Sv* sets, for example, a bulking boundary value in the SVI-constant region. The retrieval of the factors can be made on the basis of number of flocs N(t) and floc average particle size R(t). For example, when N(t) is larger and R(t) is smaller, it is judged that the load of organic matters is lower or the dissolved oxygen concentration is lower, whereas when N(t) is smaller and R(t) is larger, it is judged that the load of organic matters is high, and the thus obtained factors are output to the monitor 60.

In case of Sv(t)>Sv*, on the other hand, the tendency of the evaluation index to increase or decrease is obtained in a judge circuit 523 and at least in case of the tendency to decrease, the state of deterioration of sludge settlability is displayed on the monitor 60. Furthermore, a second factor-retrieval circuit judges whether the factor is due to the influence of floc average particle sizes or due to the influence of filamentous microorganisms, and the result of judgement is output to the monitor 60. Judgement of the tendency of evaluation index to increase or decrease and the factor can be made with a plurality of individual image information obtained at different time points of measurement. The operation judge circuit 55 judges the operators' operating system judged on the basis of the content of information displayed on the monitor 60.

The monitor 60 has at least a display function and an input function, and a result of judgement by operators is input into the monitor 60 from the input function. The input information includes selection of operating value and the set value, or desired value of control index to the selected operating value. For example, when an aeration air rate is selected as an operating value, a set aeration air rate or a desired dissolved oxygen concentration constitutes the input information. When a return sludge rate is selected as an operating value, a set return sludge flow rate or a return ratio or a desired sludge concentration in the liquid mixture in the aeration tank 1 constitutes the input information. When an excess sludge rate is selected as an operating value, a set sludge withdrawal rate or a rate of solid matters or desired sludge retention time or sludge concentration in the aeration tank constitutes the input information. Selection of these operating values and input of the set values can be made on the basis of the output information from the settlability diagnosis circuit 52, the type of filamentous microorganisms judged based on the input information and the experiences and knowledge of operators based on the results of water quality assay. When the bulking factor is retrievable from the image computation information, the set operating values for the corresponding factors or desired control index values can be changed corresponding to deviation values between the evaluation index Sv(t) and the set value Sv*.

The operation judge circuit 55 judges the input information by operators and outputs the operating conditions to the controller 70. The controller 70 operates an aeration air rate-controlling means 74, a return sludge rate-controlling means 72 or an excess sludge rate-controlling means 76 on the basis of output information from the operation judge circuit 55 so as to keep the aeration air rate, the return sludge rate or the excess sludge rate at the predetermined one. As the plant information for controlling the operating values, an inflow water rate 5A, a return sludge rate 7A, an excess sludge rate 9A, an aeration air rate 8A, an aeration tank DO 15A, a sludge concentration 15B and a return sludge concentration 7B are input into the controller 70.

In the foregoing, one embodiment of the present invention has been described, but the present invention is not limited to the foregoing disclosure. For example, the black and white parts of image g (i, g) to be processed in the image processor 30 can be reversed. In that case, the binalized information according to formulae (1) will be reversed. The reversed black-and-white image can be also obtained by changing the illumination position of image pickup unit 20, that is, by such an illumination method as to pick up scattered light of active sludge as an image, and it is also possible to extract the microorganism phase even from the thus obtained image by the above-mentioned image-processing procedure. Computation of the evaluation index Sv(t) can be made by obtaining a difference in the luminance between the liquid phase region B and the floc region Z in FIG. 4, and adding the luminance difference to the numerator term on the right side of equation (10), thereby modifying the index. The difference in the luminance therebetween is in good correlation to a difference in the density therebetween, and thus the exactness of prediction of settlability can be more improved by taking the difference into consideration.

Furthermore, the position to locate the image pickup unit 20 is not limited. For example, the image pickup unit 20 can be dipped in the inflow zone to the final settling pond 2, or can be used according to a system of continuously sampling the liquid mixture 15 from the aeration tank, the effluent liquid from the aeration tank or the return sludge 7.

In the computation of evaluation index according to the equation (10), the floc volume is used, but a total floc area can be also used. The total floc area can be calculated according to the following equation:

$$F(t) = \sum_{j=1}^{P} \left\{ \left( \sum_{j=1}^{N_j} f_i \right) / v \right\}_j \quad (13)$$

As the average floc particle size, a geometric average particle size is used, but a logarithmic average particle size based on particle size distribution can be also used.

Figure 11:
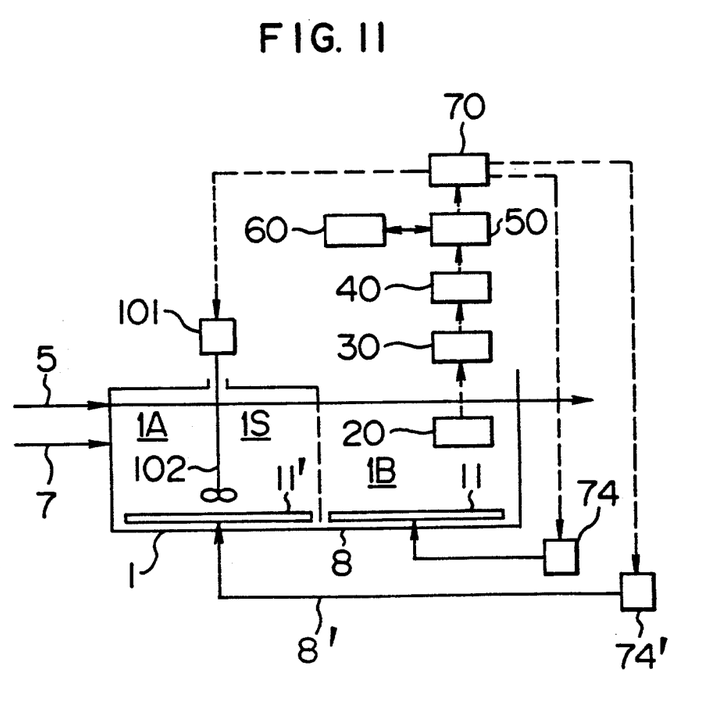
FIGS. 11 and 12 are schematic flow diagrams showing other embodiments according to the present invention.

In the foregoing embodiment, a system of controlling the aeration air rate, the return sludge rate and the excess sludge rate on the whole has been explained, but the present invention is not limited thereto. For example, as shown in FIG. 11, separate air diffusers 11' and 11 are provided at the first half stage 1A and the second half stage 1B in the aeration tank 1, respectively, and the aeration rates of air 8' and air 8 can be changed to predetermined ones by controlling the corresponding control means 74' and 74. Filamentous microorganisms that cause bulking include species whose propagation can be suppressed by controlling the aeration air rate at the first half stage in the aeration tank 1, and thus the above-mentioned modification can be applied to such filamentous microorganisms. In that case, the desired OD value must be changed between the first half stage and the second half stage. Or, such a system as to discontinue to supply the aeration air to the first half stage and actuate a driving means 101, thereby rotating a vane stirrer 102 to stir the liquid mixture can be used.

Figure 12:
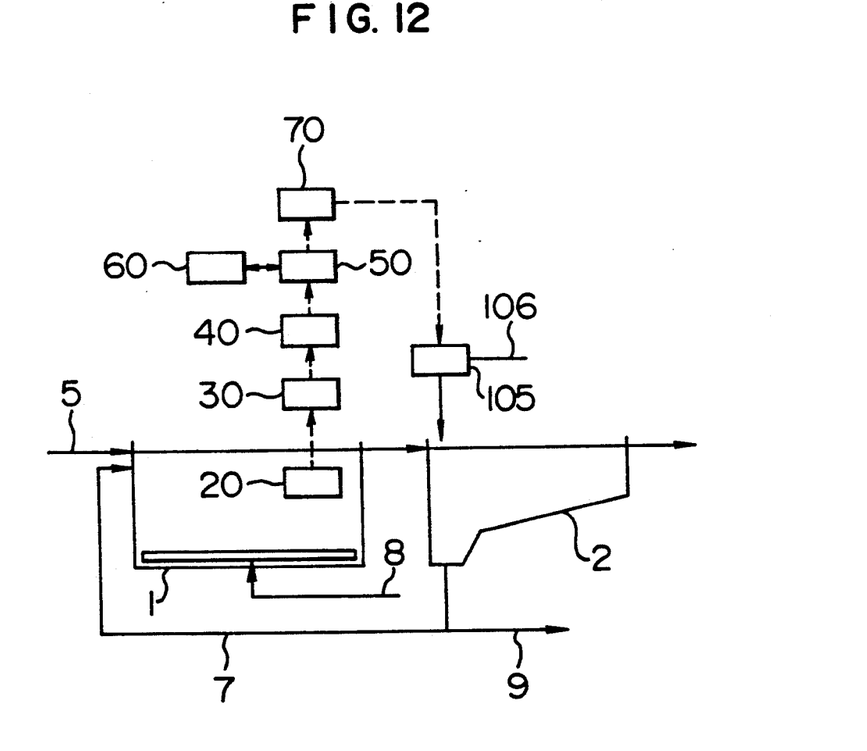

FIG. 12 shows a system of driving a supply means 105 to inject a coagulating agent 106 when a bulking is predicted. The injection point may be located in the inflow zone in the final settling pond 2, as shown in FIG. 12, or may be located in the aeration tank 1, or in the inflow water 5 or effluent water from the aeration tank 1. As the coagulating agent, PAC, aluminum sulfate, ferric chloride, quick lime, etc. can be used. Injection of the coagulating agent is preferably applied to cases that no improvement of settlability is obtained even against changed operating conditions, by setting the set value Sv* of evaluation index to a lower one than in the embodiment of FIG. 1 or by combination with FIG. 1.

Furthermore, the foregoing embodiment is directed to a process utilizing the oxidation reaction of active sludge, but the present invention is applicable to processes utilizing a reduction process or an anaerobic reaction. It is also possible to adjust the inflow water rate or the injection position, so far as a process is variable as to the inflow water rate or injection position.

Furthermore, the present invention is also applicable to processes where the floc shape depends on the operating conditions or inflow conditions, for example, as a process for predicting the settling characteristics of flocs formed in waterworks. In that case, the developed phase is a single species, and thus the concentration of turbid matters in the effluent from the settling pond can be evaluated from the particle size range of the particles failing to settle as far as the predetermined position within the residence time in the settling pond and also from the floc volume existing in the above-mentioned range, using floc particle size as the main factor. Furthermore, adjustment by a difference in the luminance between the liquid phase region and the floc region can be also made to support control of injection rate of a coagulating agent or control of stirring intensity for floc formation. To determine the settling speed of flocs means that removal of settled matters in a solid-liquid separation tank can be carried out corresponding to the settling speed. For example, in case of particle sizes of low settling speed, the sludge-removing rate is increased to promote the settling and the settling interface is lowered to reduce the ratio of upwardly moving sludge due to fluidization by stirring.

The effect of the present invention can be more improved by taking a change in viscosity into consideration, using the water temperature as a factor for evaluation index.

In the present invention the suspension states such as settling characteristics, etc. can be effectively determined by evaluation index based on the quantity of substances (sludges) suspended in a liquor, and the sludge settlability can be predicted by determining the tendency of evaluation index to increase or decrease. According to the predicted settlability, a step can be rapidly taken against possible deterioration of settlability.

What is claimed is:

1. A process for treating suspended substances in a liquor, which comprises picking up images of the substances suspended in liquor, processing the thus obtained images as pieces of pickup information, thereby determining average particle size and volume of existing coagulating microorganisms and length of existing filamentous microorganisms, determining a change in an evaluation index with time by using a ratio of length in existing filamentous microorganisms to average particle size and volume of existing coagulating microorganisms as the evaluation index, and making the thus obtained change in the evaluation index with time correspond to a correlation obtained in advance between the evaluation index and the settlability of the suspended substances, thereby predicting a precipitation state, and controlling at least one factor influencing the precipitation state on the basis of the predicted precipitation state.

2. A process according to claim 1, wherein the evaluation index is expressed as a ratio of (average particle size of coagulating microorganisms)$^n$/(length of filamentous microorganisms)/(volume of coagulating microorganisms), the settlability of the suspended substances is expressed as a volume of precipitated suspended substances per unit weight, and the change in the evaluation index with time is made to correspond to the correlation, thereby predicting the precipitation state of the suspended substances.

3. A process according to claim 1, wherein the evaluation index is expressed as a ratio of (average particle size of coagulating microorganisms)$^2$/(length of filamentous microorganisms)/(volume of coagulating microorganisms), the settlability of the suspended substances is expressed as a volume of precipitated suspended substances per unit weight, and the change in the evaluation index with time is made to correspond to the correlation, thereby predicting the precipitation state of the suspended substances.

4. A process for treating substances suspended in a liquor, which comprises determining an amount of existing suspended coagulating microorganisms and a amount of existing suspended filamentous microorganisms in a liquid suspension containing the coagulating microorganisms and the filamentous microorganisms by image processing, thereby obtaining a ratio of the amount of the existing suspended coagulating microorganisms to the existing suspended filamentous microorganisms, repeating the determination at time intervals a plurality of times, thereby obtaining a rate of change in the ratio with time and predicting a future settling state of the microorganisms, and controlling at least one factor influencing the settling state of the microorganisms on the basis of the predicted future settling state.

5. A process according to claim 4, wherein the ratio is a ratio of (average particle size of coagulating microorganisms)$^2$/(length of filamentous microorganisms/volume of coagulating microorganisms).

6. A process for treating suspended substances in a liquor according to claim 1 or 4, wherein the substances suspended in the liquor are active sludge.

* * * * *